United States Patent [19]

Schreiner

[11] Patent Number: 5,904,670
[45] Date of Patent: May 18, 1999

[54] CATHETERS AND METHODS FOR GUIDING DRUGS AND OTHER AGENTS TO AN INTENDED SITE BY DEPLOYABLE GROOVES

[75] Inventor: Dale L. Schreiner, Cologne, Minn.

[73] Assignee: XRT Corp., St. Paul, Minn.

[21] Appl. No.: 08/627,006

[22] Filed: Apr. 3, 1996

[51] Int. Cl.$^6$ .................................................. A61M 25/00
[52] U.S. Cl. ........................ 604/280; 604/104; 604/264; 604/107
[58] Field of Search ..................................... 606/191, 194, 606/198, 200; 604/19, 27, 30, 48, 93, 96, 104–109, 164, 166, 264, 280, 158–160

[56] References Cited

U.S. PATENT DOCUMENTS

| | | |
|---|---|---|
| 3,472,230 | 10/1969 | Fogarty . |
| 3,821,956 | 7/1974 | Gordhamer . |
| 3,938,530 | 2/1976 | Santomieri . |
| 3,952,747 | 4/1976 | Kimmell, Jr. . |
| 4,430,083 | 2/1984 | Ganz et al. . |
| 4,488,877 | 12/1984 | Klein et al. . |
| 4,494,531 | 1/1985 | Gianturco . |
| 4,636,195 | 1/1987 | Wolinsky . |
| 4,643,184 | 2/1987 | Mobin-Uddin . |
| 4,693,243 | 9/1987 | Buras . |
| 4,706,671 | 11/1987 | Weinrib . |
| 4,737,141 | 4/1988 | Spits . |
| 4,790,812 | 12/1988 | Hawkins, Jr. et al. . |
| 4,793,348 | 12/1988 | Palmaz . |
| 4,813,925 | 3/1989 | Anderson, Jr. et al. . |
| 4,824,436 | 4/1989 | Wolinsky . |
| 4,873,978 | 10/1989 | Ginsburg . |
| 4,874,360 | 10/1989 | Goldberg et al. . |
| 4,878,893 | 11/1989 | Chin . |
| 4,887,996 | 12/1989 | Bengmark . |
| 4,950,258 | 8/1990 | Kawai et al. . |
| 4,957,479 | 9/1990 | Roemer . |
| 4,986,814 | 1/1991 | Burney et al. . |

(List continued on next page.)

OTHER PUBLICATIONS

Eichelter, M.D., et al., *A New Experimental Approach to Prophylaxis of Pulmonary Embolism*, pp. 455–456, Nov.–Dec., 1967.

Eichelter, M.D., t al., *Prophylaxis of Pulmonary Embolism: A New Experimental Approach With Initial Results*, Arch. Surg–vol. 97, Aug. 1968, pp. 348–356.

PROLYSER™ Product Information Package; 3 pages, CORDIS®, ©Cordis International SA, Jan. 1995.

DISPATCH™ Product Information Brochure; 4 pages, SCIMED® Life Systems, Inc., ©1994 SCIMED Life Systems, Inc.

*Primary Examiner*—Ronald Stright, Jr.
*Attorney, Agent, or Firm*—Merchant, Gould, Smith, Edell, Welter & Schmidt, P.A.

[57] ABSTRACT

Catheters for delivering drugs or other agents within a lumen, such as an artery or vein, are disclosed. In one embodiment, a catheter comprises an outer shaft with a lumen extending longitudinally therethrough. An inner shaft is slidably received within the outer shaft. A distal portion of the shaft comprises a plurality of grooved delivery members having a non-deployed position wherein the delivery members lie within and are compressed by the outer shaft, and a deployed position wherein the delivery members extend beyond the outer shaft. In the deployed position, the delivery members flare outward at an angle, beyond the diameter of the outer shaft to bear against a site of interest, which can be a thrombus or a vessel wall, for example. Drugs or other agents can be conveyed to the delivery members through a space between the inner and outer shafts. In another embodiment, distal portions of the grooved delivery members are coupled to an inner shaft at a first location and proximal portions of the grooved delivery members are coupled to an outer shaft at a second location. Movement of the inner and outer shafts with respect to each other to bring the first and second locations together causes the delivery members to buckle outward, deploying the members. Methods of drug delivery are also disclosed.

11 Claims, 8 Drawing Sheets

U.S. PATENT DOCUMENTS

| | | |
|---|---|---|
| 4,994,069 | 2/1991 | Ritchart et al. . |
| 4,997,435 | 3/1991 | Demeter . |
| 5,034,001 | 7/1991 | Garrison et al. . |
| 5,035,706 | 7/1991 | Giantureo et al. . |
| 5,041,093 | 8/1991 | Chu . |
| 5,062,829 | 11/1991 | Pryor et al. . |
| 5,087,244 | 2/1992 | Wolinsky et al. . |
| 5,133,733 | 7/1992 | Rasmussen et al. . |
| 5,147,379 | 9/1992 | Sabbaghian et al. . |
| 5,152,777 | 10/1992 | Goldberg et al. . |
| 5,160,342 | 11/1992 | Reger et al. . |
| 5,181,911 | 1/1993 | Shturman . |
| 5,221,261 | 6/1993 | Termin et al. . |
| 5,242,452 | 9/1993 | Inoue . |
| 5,256,146 | 10/1993 | Ensminger et al. . |
| 5,267,960 | 12/1993 | Hayman et al. . |
| 5,279,565 | 1/1994 | Klein et al. .............................. 604/105 |
| 5,304,120 | 4/1994 | Crandell et al. . |
| 5,306,250 | 4/1994 | March et al. . |
| 5,318,576 | 6/1994 | Plassche, Jr. et al. . |
| 5,324,304 | 6/1994 | Rasmussen . |
| 5,336,178 | 8/1994 | Kaplan et al. . |
| 5,342,348 | 8/1994 | Kaplan . |
| 5,350,398 | 9/1994 | Pavcnik et al. . |
| 5,370,657 | 12/1994 | Irie . |
| 5,383,887 | 1/1995 | Nadal . |
| 5,413,586 | 5/1995 | Dibie et al. . |
| 5,415,630 | 5/1995 | Gory et al. . |
| 5,509,900 | 4/1996 | Kirkman . |
| 5,527,280 | 6/1996 | Goetz . |
| 5,713,853 | 2/1998 | Clark et al. ............................. 604/104 |

CATHETERS AND METHODS FOR GUIDING DRUGS AND OTHER AGENTS TO AN INTENDED SITE BY DEPLOYABLE GROOVES

FIELD OF THE INVENTION

Drug delivery catheters and, more particularly, drug delivery catheters with self-expanding drug delivery portions comprising grooves which guide drugs or other agents towards an intended site, are disclosed. Examples of possible sites include the walls of lumens or vessels such as arteries or veins, or obstructions in such lumens or vessels, such as a thrombus. Methods of drug delivery are also disclosed.

BACKGROUND OF THE INVENTION

It is often necessary to deliver drugs to a particular site within a body. For example, catheters are used to deliver drugs or other agents to lumens or vessels within the cardiovascular system, the urethra, bladder, prostate, rectum and central nervous system, such as the spinal cord.

Thrombosis, the formation of a clot or thrombus in the cardiovascular system from the constituents of blood, is a potentially life threatening condition. Thrombosis can develop in any part of the cardiovascular system, but is most common in veins, particularly the deep veins in the leg. Thrombosis can result from a variety of causes including poor circulation, trauma, prolonged bed rest, or hip surgery, for example. In the arteries, thrombosis can be caused by arteriosclerosis. Thrombosis can develop in cerebral vessels, as well.

If a portion of the thrombus separates and is transported through the cardiovascular system, it can cause an embolism, or blockage of a blood vessel. A thrombus in a deep vein in the leg can cause a pulmonary embolism. A thrombus in a coronary artery can cause myocardial infarction. Similarly, a thrombus in a cerebral artery can cause cerebral infarction.

During the early development of thrombosis, up to about seven days, the thrombus is soft and can be treated by a variety of techniques. Drug delivery catheters have been used to provide thrombolytic drugs or agents such as urokinase, streptokinase and recombinant tissue type plasminogen activator (rTPA), directly onto and into a thrombus. The FasTracker infusion catheter from Target Therapeutics®, for example, comprises a catheter shaft with a drug delivery lumen extending through the shaft. A drug delivery port is located at the distal end of the shaft. To dissolve a thrombus, the FasTracker can be advanced through the thrombus and then withdrawn back through the thrombus as a thrombolytic drug or agent is delivered into the thrombus. This process can be repeated several times. Such a catheter has several disadvantages. For example, it can be difficult to center within the thrombus. In addition, as the thrombus dissolves, the catheter could be drawn to one portion of the vessel by gravity, preventing even delivery of drug to other portions of the thrombus. A catheter which could apply thrombolytic agents evenly to all portions of a thrombus would be advantageous.

In alternative treatments, a pulse spray of a lytic agent, such as urokinase, has been directed onto soft thrombi to mechanically break up and dissolve them. High pressure water has also been directed onto the thrombus to destroy it. The thrombus can also be broken by a laser or a drill. The broken or dislodged portions of the thrombus may be aspirated through a catheter so that they cannot migrate and obstruct other vessels of the cardiovascular system. Results have been mixed, with some treatments damaging tissue, causing another thrombotic or stenotic process. A surgical procedure may be required to remove the thrombus, as well.

It has been found that the application of lytic agents to a clot under pressure provides improved results over diffusion. Blinc, A., et al., "Dependence of Blood Clot Lysis on the Mode of Transport of Urokinase into the Clot—A Magnetic Resonance Imaging Study In Vitro," Thrombosis and Haemostosis, 65(5) 549–552 (1991). U.S. Ser. No. 08/534,856, filed on Sep. 27, 1995, assigned to the assignee of the present invention, discloses driving a drug or other agent through the thrombus by pressure, withdrawing and filtering the thrombic material and delivered drug, and recycling the drug.

In other cardiovascular applications, various types of agents are being investigated for use in preventing restenosis of an artery after percutaneous transluminal coronary angioplasty (PTCA) or percutaneous transluminal angioplasty (PTA). Heparin, an anticoagulant and inhibitor of arterial smooth muscle proliferation, is one such drug. Dexamethasone may also prevent smooth muscle proliferation. Other drugs and agents are being investigated for efficacy, as well. Such drugs can be delivered before or after the angioplasty procedure. The delivery of lytic agents such as urokinase, streptokinase and recombinant tissue type plasminogen activator (rTPA) to dissolve plaque in arteries and veins is also being investigated.

Because of blood flow through the artery, drugs delivered to the site of an angioplasty procedure, for example, can be rapidly dissipated and removed from the delivery site before they can be absorbed in sufficient quantities to become effective. Catheters have therefore been developed to directly deliver drugs to the desired site and maintain them there. For example, U.S. Pat. No. 5,087,244 to Wolinsky et al., discloses a catheter with a flexible balloon having a plurality of minute openings. The balloon can be inflated by heparin. As the walls of the balloon contacts the arterial wall, the heparin exits the balloon, directly on the walls. The balloon can block the perfusion of blood distal to the delivery site, depriving tissue of needed blood. This limits the amount of time available for drug delivery. The inflation of the balloon can also damage the arterial wall, promoting restenosis. In addition, since the balloon is inflated by the heparin, heparin can leak out before the arterial wall is contacted, wasting the drug. The balloon also needs to be deflated prior to removal or to allow blood flow. The pressure required to deflate the balloon could draw blood into the balloon, preventing further use of the catheter until the blood has been removed.

U.S. Pat. No. 4,824,436, also to Wolinsky, discloses a drug delivery catheter comprising a pair of occlusion balloons for securing the catheter in position and isolating a region of the artery which has been opened by PTCA, and a drug delivery conduit for delivering heparin under pressure into the region isolated by the occlusion balloons. The pressure of the heparin forces the heparin to coat and penetrate the arterial tissue. This configuration presents the similar perfusion problems to those discussed above. The heparin, therefore, is only delivered for 5–60 seconds, which may be inadequate for sufficient absorption.

U.S. Pat. No. 5,336,178 to Kaplan et al., discloses a catheter with drug delivery ribs which are brought into contact with the walls of the body lumen by an inflatable balloon. A series of ports in the catheter shaft can be provided proximal to the balloon to allow for perfusion of blood through the catheter shaft. As above, inflation of the balloon can damage the wall of the lumen.

One commercially available drug delivery product is the DISPATCH™ from Scimed. The DISPATCH™ includes an inflatable polyurethane coil which provides a path for blood to flow and defines regions proximate the wall of the vessel into which drug is delivered. While apparently allowing for significant perfusion, the device is complex and therefore difficult to use and manufacture. The inflatable coil can also prevent portions of the artery from being exposed to the drug and block perfusion to side branch arteries.

It is known that the velocity of fluid flow through a tube varies across the axial cross-section of the tube. The velocity is maximum at the center of the tube and approaches zero at the walls. In an artery or a vein, blood flow is very slow in the region proximate the walls. If drugs or other agents could be effectively delivered proximate the walls, the blood flow can atraumatically carry the delivered drug or agent over the site of interest. The delivered drug or agent would also not dissipate as rapidly as drug delivered to the center of the vessel. Less drug could then need to be delivered, shortening procedures and decreasing their cost.

U.S. Ser. Nos. 08/483,201, and 08/488,216, now U.S. Pat. No. 5,713,853 filed on Jun. 7, 1995 and assigned to the assignee of the present invention, disclose drug delivery catheters with self-expanding drug delivery portions comprising a plurality of resilient members. A shaft, sleeve or other restraining means compresses the drug delivery portion until the drug delivery portion is proximate the site of interest. The restraining means is then retracted or removed, allowing the drug delivery portion to expand radially to bear against the wall of the vessel. Drugs or other agents can then be delivered through lumens in each member.

Drugs and other agents are delivered to lumens, vessels and cavities in other portions of the body, such as the urethra, bladder, prostate, rectum, bile duct, pancreatic duct and central nervous system, such as along the spinal column, to treat a variety of conditions, as well.

SUMMARY OF THE INVENTION

A catheter is disclosed comprising self-expandable delivery members with grooves which are compressed while the catheter is advanced to a site within a lumen, such as an artery or a vein, for example. When deployed at a desired site, the delivery members are released to bear against the site, which can be an obstruction in a lumen, such as a thrombus, or the walls of the lumen itself.

In accordance with one embodiment of the invention, a catheter for delivering drugs or other agents within a lumen is disclosed comprising an outer shaft having a lumen extending longitudinally therethrough and an inner shaft slidably received within the lumen of the outer shaft. The inner shaft has a distal portion and a proximal portion. The distal portion comprises a plurality of grooved resilient delivery members. The delivery members have a non-deployed position compressed by the outer shaft when the delivery members are within the outer shaft and a deployed position when the delivery members extend out of the outer shaft, wherein in the deployed position the delivery members flare outward beyond the outer shaft at an angle. The inner and outer shafts define a space between them through which the drug or agent is conveyed to the grooves of the delivery members.

In accordance with another embodiment of the invention, a catheter is disclosed comprising an outer shaft having a lumen extending longitudinally therethrough and an inner shaft slidably received within the lumen of the outer shaft. A plurality of grooved delivery members are provided having distal portions coupled to the inner shaft at a first location and proximal portions coupled to the outer shaft at a second location. The first location is proximal to the second location. The delivery members have a length such that the delivery member has a non-deployed position when the first and second locations are separated by a distance approximately equal to the length of the delivery member, and a deployed position when the first and second locations are separated by a distance less than the length of the delivery member. The delivery members have central portions between the proximal and distal portions which extend outward beyond the outer shaft in the deployed position.

A catheter for delivering drugs or other agents to a site within a lumen is also disclosed comprising a delivery portion having a first shaft with a distal portion and at least one resilient grooved delivery member at the distal portion. The delivery member has a deployed position wherein the delivery member bears against the site and a non-deployed position wherein the delivery member does not bear against the site. Means are provided for deploying the delivery member from the non-deployed position to the deployed position. Means are also provided for conveying a drug or agent through the catheter, to the delivery member.

In accordance with another embodiment of the invention, a method of delivering drugs or other agents to a site within a lumen is disclosed comprising advancing a catheter having grooved delivery members to the site; deploying the delivery members such that they bear against the site; conveying drugs or other agents through the catheter; and guiding the conveyed drugs or agents from the catheter to the site by the grooves.

DESCRIPTION OF THE INVENTION

Figure 1:
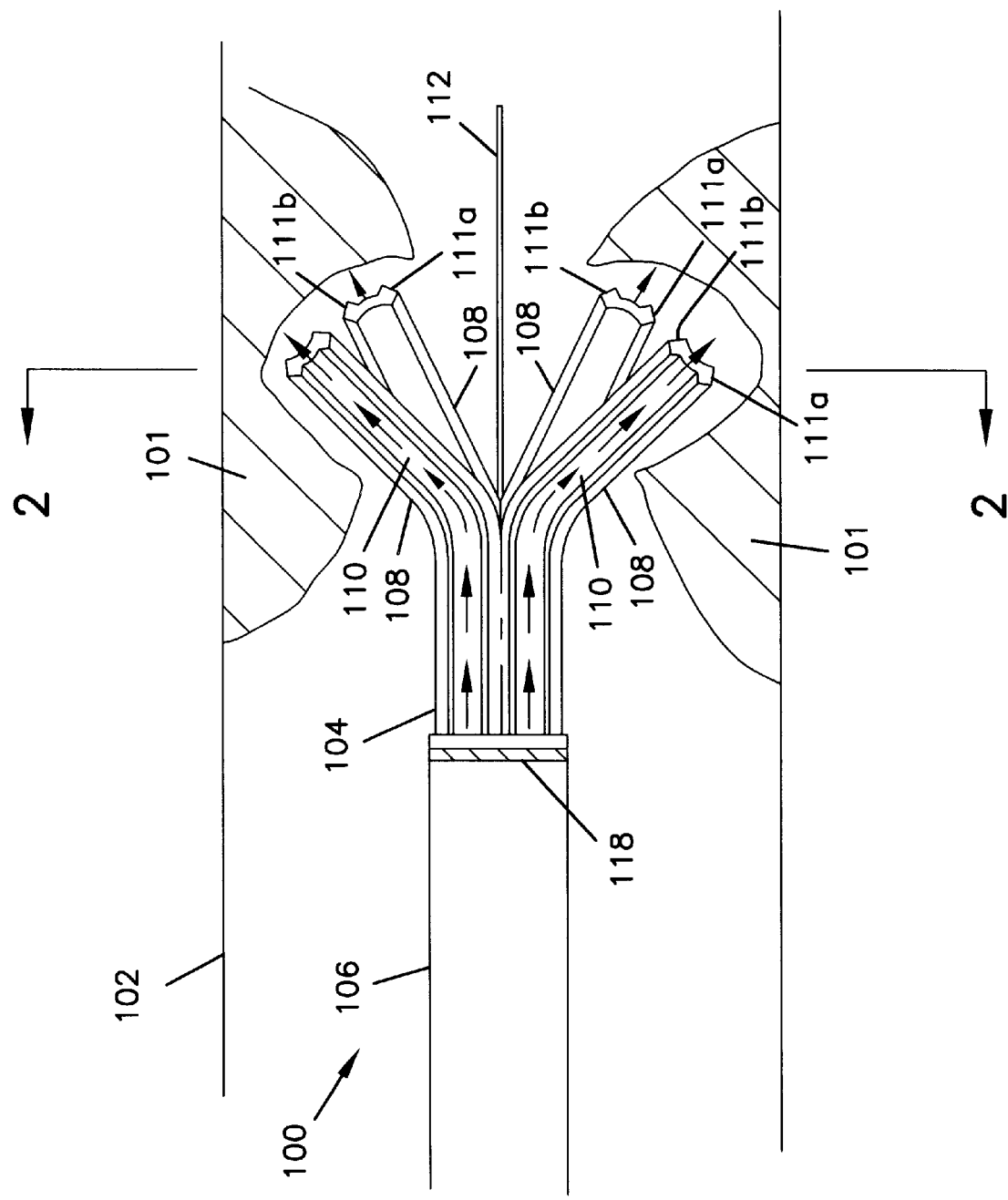
FIG. 1 is a side view of a catheter in accordance with one embodiment of the present invention, deployed within a thrombus in an artery.

FIG. 1 is a side view of a catheter 100 in accordance with one embodiment of the present invention, deployed to deliver drugs or other agents to a thrombus 101 within a cerebral artery 102, for example. The thrombus 101 is shown partially dissolved, as described below. The catheter comprises an inner shaft 104 slidably received within an outer shaft 106. The inner shaft 104 has a distal portion comprising one or more resilient delivery members 108 which when deployed flare outward from the inner shaft 104 at an angle, beyond the diameter of the outer shaft 106 and towards the walls of the artery 102. Each delivery member 108 comprises a longitudinal groove 110. The groove 110 may be defined by walls 111a, 111b. Four delivery members 108 are provided in this embodiment. The catheter 100 is preferably advanced to the site of interest over a guidewire 112. The guidewire 112 is preferably received within a lumen 114 extending longitudinally through the inner shaft 104. A front view of the lumen 114 is shown in FIG. 2.

Figure 2:
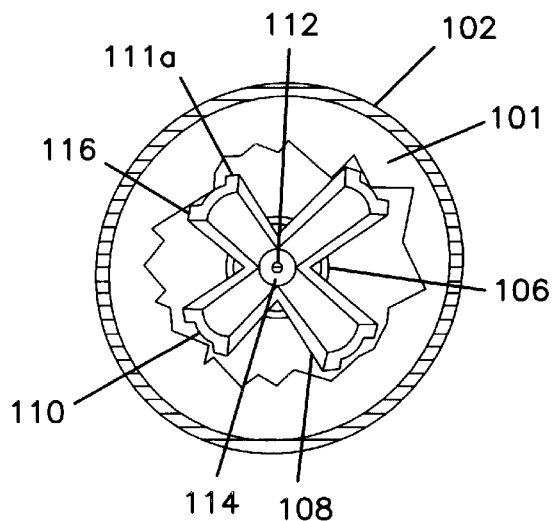
FIG. 2 is a front view of the catheter through line 2—2 of FIG. 1.

FIG. 2 is a front view of the deployed catheter 100 and the artery 102 along line 2—2 of FIG. 1, through the thrombus 101. The walls 111a, 111b of the deployed delivery members 108 are shown bearing against the wall of the thrombus 101. The distal edge of the outer shaft 106 is also shown.

Figure 3:
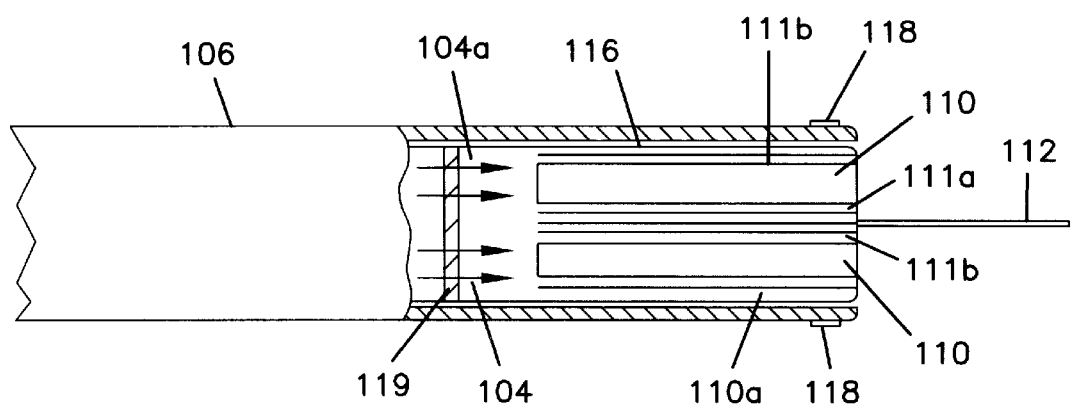
FIG. 3 is a partial cross-sectional view of the catheter of FIG. 1, in a non-deployed position.

FIG. 3 is a partially cutaway side view of the catheter 100 of FIG. 1, in a non-deployed position within the artery 102. The delivery members 108 lie completely within the outer shaft 106, a portion of which is shown in cross-section. In this embodiment, the outer shaft 106 compresses the delivery members 108, maintaining them within the inner diameter of the outer shaft 106 while the catheter 100 is stored, advanced to a desired site and, optionally, when the catheter 100 is withdrawn. When the distal end of the catheter 100 is properly positioned at the site of interest, as discussed below, the delivery members 108 can be released by retracting the outer shaft 106, allowing the delivery members 108 of the distal portion to flare outward beyond the outer diameter of the outer shaft 106. Alternatively, the inner shaft can be advanced to release the delivery members 108.

The outer wall of the inner shaft 104 and the inner wall of the outer shaft 106 preferably define a space 116 extending from the proximal end of the catheter 100 through the catheter 100 to the delivery members 108 through which drugs are conveyed through the catheter 100 to the grooves 110.

The inner shaft 104 preferably includes a smooth portion 104a proximal to the delivery members 108. A smooth shaft causes less friction with the delivered drug or agent, which can slow fluid flow. In a catheter of about 145 cm, for example, the grooves 110 preferably extend about 20 cm from the distal tip of the inner shaft 104. The remainder of the inner shaft 104 is preferably smooth. After traversing the length of the outer shaft 106, the drugs are channeled into the grooves 110 of the delivery members 108. The drugs then follow the grooves to the site of interest, as shown by the arrows in FIG. 1.

If desired, however, the grooves 110 can extend the entire length of the inner shaft 104. In that case, a larger space 116 may be required to achieve an adequate flow rate. While the term "drug" is generally used hereafter, it is understood that other agents can be delivered as well.

The catheter 100 in accordance with the present invention can have an outer diameter of approximately 0.038 inches, for example. This is small enough to be advanced through, and to treat conditions in, cerebral arteries, which typically have diameters ranging from about 1.0–4.5 mm. The inner diameter of the outer shaft 106 is preferably about 0.031 inches. The outer diameter of the smooth portion of the inner shaft is preferably about 0.026 inches, defining the space 116 with a height of about 0.005 inches. The inner diameter of the inner shaft 104 is preferably about 0.017 inches. The outer diameters of the walls 111a, 111b of the grooves 110 are preferably about 0.029 inches. The outer diameters of the grooves 110 themselves are preferably about 0.023 inches.

The height of each wall 111a, 111b from the inner diameter is preferably about 0.006 inches. The width of each groove 108 is preferably about 0.009 inches. The length of the grooved distal portion of the inner shaft 104 is preferably about 20 cm. The length of the expandable delivery members 108 is about 5.0 mm. The dimensions of the catheter 100 may also vary dependent upon the diameter of the intended site. For example, a larger diameter catheter with longer delivery members 108 may be desired for a site with a larger diameter.

Drugs can be delivered through lumens in the inner or outer shaft as well. Such shafts could be formed in a multi-lumen extrusion process. Such multi-lumen shafts could, however, increase the outer diameter of the catheter 100, making it inappropriate for certain applications, such as within the smaller cerebral arteries. Catheters with multiple drug delivery lumens are disclosed in U.S. Ser. No. 08/483, 201, now abandoned and U.S. Ser. No. 08/488,216, now U.S. Pat. No. 5,713,853 incorporated by reference, herein.

The number of delivery members 108 can vary. The preferred number can depend on the diameter of the vessel where the drug is to be delivered. For example, four delivery members 108 are preferably provided in this embodiment, which will enable an even distribution of the delivered drug to the thrombus 101 in a cerebral artery 102. Additional delivery members 108 could be preferred for larger vessels, such as the coronary arteries or deep veins in the leg.

The angle of the flare of the delivery members 108 with respect to a longitudinal axis of the inner shaft 104 when fully deployed outside of a lumen is preferably about 90°. The preferred angle of 90° ensures that the delivery members 108 will rotate through the entire cross-section of the vessel or lumen, even if the catheter 100 is not centered within the thrombus or even if the delivery members 108 are deployed within a curved portion of the vessel or lumen. The delivery members 108 preferably have a length such that when fully expanded within the vessel, the distal portions of the delivery members bear against the vessel walls.

The outer shaft 106 preferably includes a radiopaque band 118 of gold, tantalum, platinum or iridium, for example, proximate its distal end, to assist in tracking the progress of the catheter on a fluoroscope during a procedure, as is known in the art. The inner shaft 104 may also include a radiopaque band 119 to assist in determining whether the outer shaft 106 has been sufficiently retracted. Preferably, the marker band 119 is positioned about 15 mm from the distal end of the delivery members 108. When the band 118 is approximately aligned with the band 119, the outer shaft 106 has been sufficiently retracted.

The distal portion of the inner shaft 104, particularly the delivery members 108, is preferably a soft, flexible, resilient material which can be advanced through the turns of the vascular system and be deployed without damaging the vessel walls. The material must also be capable of being heat set in an expanded position and compressed by the outer shaft when not deployed. Despite its softness, however, it must have sufficient pushability and torqueability to respond to the control of the surgeon. Low density polyethylene (LDPE), such as LDPE 640 resin from The Dow Chemical Company, is preferred. Typical property values for LDPE 640 appear below:

| RESIN PROPERTIES | | TEST ASTM METHOD | VALUES |
|---|---|---|---|
| Melt Index g/10 min. | | D 1238 | 2.0 |
| Density, g/cc | | D 792 | 0.922 |
| Tensile Yield, psi (MPa) | | D 638 | 1600(11) |
| Ultimate Tensile, psi (MPa) | | D 638 | 1600(11) |
| Ultimate Elongation, % | | D 638 | 600 |
| BLOWN FILM PROPERTIES @ 1.5 MIL | | | |
| Dart Impact, g | | D 1709 | 100 |
| Elmendorf Tear, g | MD | D 1922 | 400 |
| | CD | | 275 |
| Tensile Yield, psi (MPa) | MD | D 882 | 1600(11) |
| | CD | | 1550(10.7) |
| Ultimate Tensile, psi (MPa) | MD | D 882 | 3300(22.7) |
| | CD | | 2700(18.6) |
| Ultimate Elongation, % | MD | D 88.2 | 325 |
| | CD | | 575 |
| Gloss, 45° | | D 2457 | 65 |
| Haze, % | | D 1003 | 6 |
| Coefficient of Friction | | D 1894 | 0.8 |

The smooth, proximal portion of the inner shaft 104 is preferably a stiffer material than the delivery portion, for improved pushability and torqueability. The smooth portion can be high density polyethylene (HDPE), for example. A suitable HDPE is Petrothene® LM 6007-00 from Quantum Chemical Co., Cincinnati, Ohio. The two portions of the inner shaft 104 can be connected by adhesive or thermal bonding, as is known in the art. Typical property values for Petrothene® LM6707-00 appear below:

| PROPERTY | ASTM TEST METHOD | VALUE |
|---|---|---|
| Density, g/cm$^3$ | D 1505 | 0.960+ |
| Melt Index, g/10 min. | D 1238 | 0.7 |
| Tensile Strength @ Break, psi | D 638 | 4,400 |
| Elongation @ Break, % | D 638 | >600 |
| Flexural Modulus, psi | D 790 | 220,000 |
| Tensile Impact, ft-lb/in. | D 1822 | 100 |
| Low Temperature Brittleness, $F_{50}$ C° | D 746 | <-76 |
| Heat Deflection Temperature, @ 66 psi, °C. | D 648 | 78 |
| Vicat Softening Point, °C. | D 1525 | 125 |
| Hardness, Shore D, °C. | D 2240 | 68 |

For adequate flexibility and to protect vessel walls, the distal portion of the outer shaft 106 is also preferably a softer material than the proximal portion. The material of the distal portion of the outer shaft 106 should also have an elongation appropriate to prevent excessive stretching of the outer shaft 106 when the outer shaft is moved with respect to the inner shaft 104. Excessive stretching could impede release of the delivery members 108.

A blend of about 60% LDPE, 30% HDPE and 10% ethyl vinyl acetate (EVA) is preferred for the distal portion of the outer shaft. The LDPE and EVA are softer materials. Sufficient tracking is provided by the HDPE. ELVAX 750 from DuPont Co., for example, is an appropriate EVA. The LDPE and HDPE described above may be used, as well. Typical property values for ELVAX 750 appear below:

| | | |
|---|---|---|
| Melt Index dg/min ASTM-D1238 | | 7.0 |
| Vinyl Acetate, wt. % TGA | | 9.0 |
| Density, kg/m$^3$ (g/cm$^3$) ASTM-D792 | | 930(0.930) |
| Tensile Strength MPa (psi) ASTM-D638 | | |
| (Test Specimen = | -20° C. | 21(3,100) |
| ASTM D638, type IV; | 23° C. | 15(2,200) |
| crosshead speed = | 49° C. | 9.6(1,400) |
| 5.1 cm (2 in/min) | | |
| Elongation, % ASTM D638 | | |
| (Test Specimen = | -20° C. | 450 |
| ASTM D638, type IV; | 23° C. | 600 |
| crosshead speed = | 49° C. | 550 |
| 5.1 cm (2 in/min) | | |
| Vicat Softening Temp. ASTM-D1525 | | 73(167) |
| Flexural Modulus MPa (psi) ASTM D790 | | |
| | -20° C. | 363(52,500) |
| | 23° C. | 86(12,500) |
| | 49° C. | 6(6,700) |
| Stiffness MPa (psi) ASTM-D747 | | |
| | -20° C. | 205(29,700) |
| | 23° C. | 74(10,800) |
| Hardness Shore ASTM-D2240 | | |
| | Scale A | 95 |
| | Scale D | 47 |
| Brittleness Temp. ASTM-D746 | | |
| | ° C. | <-100 |
| | ° F. | <-148 |
| Compression Set, % ASTM-D395, Method B | 10 days at 25° C. | 46 |
| | 22 hrs. at 70° C. | 74 |
| Tensile Impact, kJ/m$^2$ (ft-lb/-in$^2$) ASTM-D1822 | | |
| | -20° C. | 305(145) |
| | 23° C. | 400(190) |

The distal portion of softer material of the outer shaft 106 preferably has a length of about 18 cm, for example. The two portions of the outer shaft can be connected by adhesive or thermal bonding, as is known in the art.

The materials preferred for the inner shaft 104 and the outer shaft 106 also slide easily with respect to each other. To further ease the movement of one shaft with respect to the other, a lubricous coating of silicone (not shown) for example, is preferably provided between the inner shaft 104 and outer shaft 106.

Other non-thrombogenic materials which can be used for the inner and outer shaft include thermoplastic elastomer resins such as polyether block amide (PEBA), polytetrafluoroethylene (PTFE), polyester elastomers, polyethylene, fluorinated ethylene propylene (FEP), polyimide and all the known grades of polyethylene such as linear low density polyethylene, LDPE, HDPE and ultra high density polyethylene. The proximal portions of the inner shaft 104 and outer shaft 106 could be steel or nitinol, as well, as long as it is flexible enough.

If the preferred materials for the outer shaft 106 and the inner shaft 104 are not rigid enough to be easily advanced along the guidewire 112 through a guide catheter, a reinforcing sleeve of stainless steel, titanium, or titanium nickel, for example, may be provided within the guidewire lumen 114. Such a reinforcing sleeve may extend from the proximal end of the catheter 100, more than half the length of the catheter up to about 12 inches or about 30 mm from the distal end of the inner shaft 104.

Other means of reinforcing the catheter can be used as well, as is known in the art. For example, the outer shaft 106 can be reinforced instead of the shaft 104. A rigid wire or stylet can also be embedded within either shaft 106, 104. Irradiation of the shafts with an electron beam to increase the cross-linking and hence the stiffness of the polymeric material, can also be used. A harder material can also be used for the outer shaft 106 or inner 104 than those preferred above, in which case the distal portion of the sleeve or shaft may need to be "necked down" to decrease its outer diameter, increasing its flexibility. This technique could be used instead of providing different materials for the distal and proximal portions of the outer shaft 106.

Figure 4:
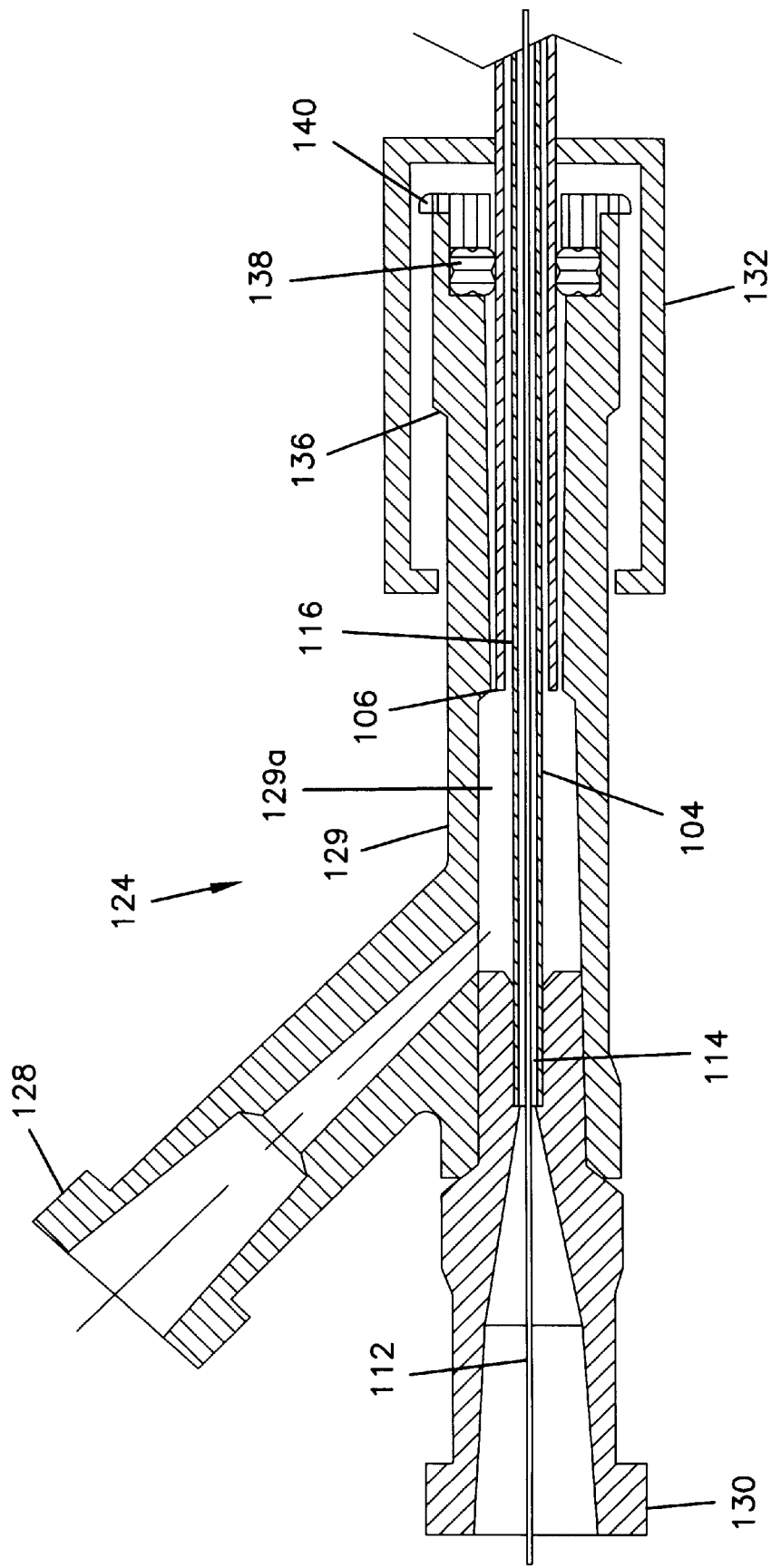
FIG. 4 is a cross-sectional view of a manifold for use with the catheter of FIG. 1.
Figure 5:
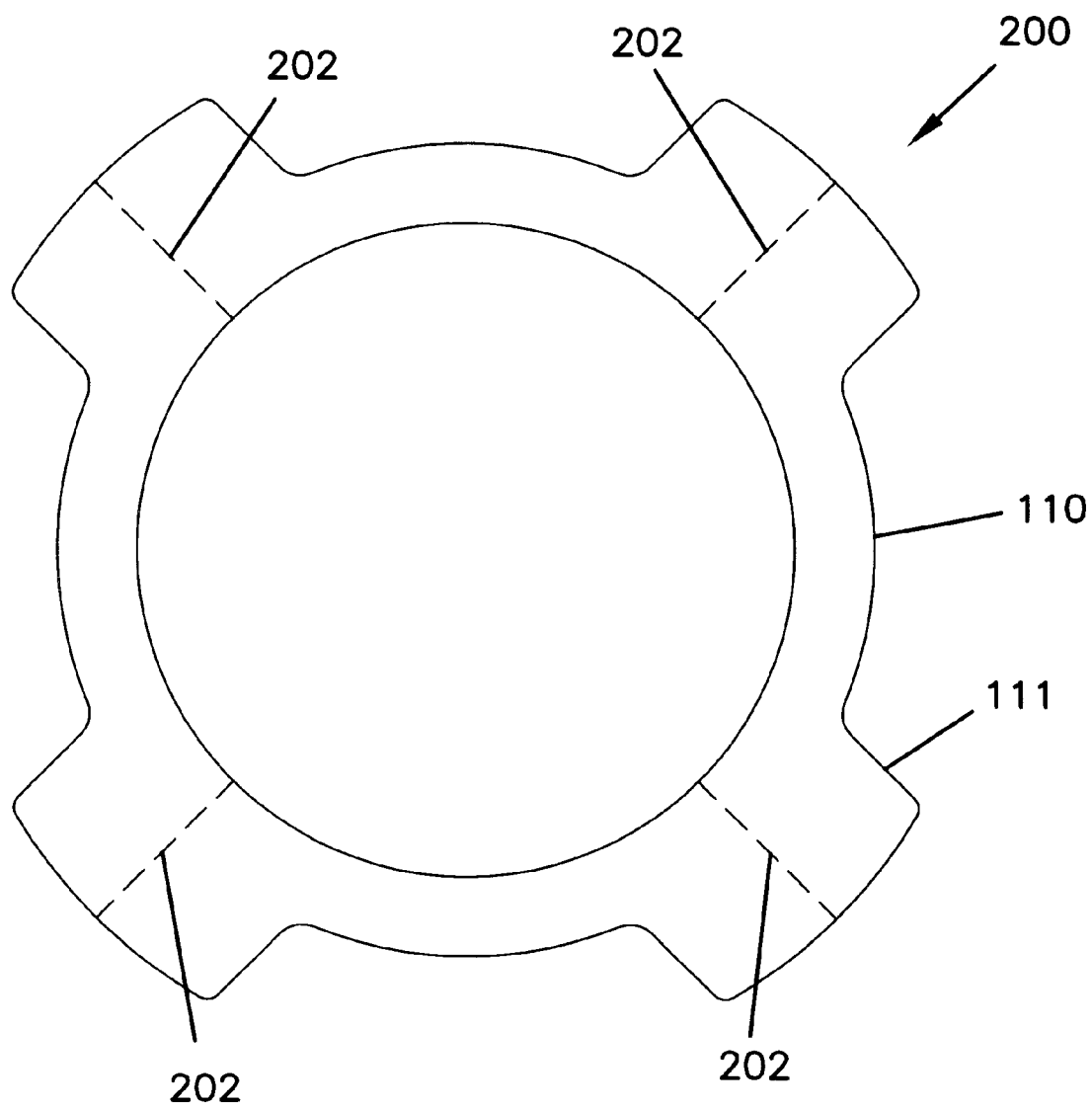
FIG. 5 is a front view of a shaft from which grooved delivery members of the catheter of FIG. 1 can be formed.

FIG. 4 is a cross-sectional view of the proximal portion of the catheter 100, including a manifold 124 for introducing a drug or other agent into the space 116 between the outer and inner shafts 106, 104. The drug is supplied from a drug infusion unit or a syringe (not shown) through a first port 128 depending from a sleeve 129. The guidewire 112 can extend through a second port 130. A collar 132 at the proximal end of the catheter 100 is attached to the outer shaft 106 to advance or retract the outer shaft. The outer shaft 106 is adhesively bonded, for example, to the collar 132.

A seal, such as an O-ring 138 of latex or silicone, for example, is preferably provided between the manifold and proximal portion of the outer shaft 106 to prevent leakage. A seal cap 140 secures the seal 138 in place. The seal cap 140 can also act as a stop engaging the collar 132 to prevent excessive retraction of the outer shaft 106. The outer shaft 106 is retracted by holding the sleeve 129 stationary and withdrawing the collar 132 a sufficient distance so that the distal portion of the outer shaft 106 is no longer compressing or restraining the delivery members 108. As discussed above, this can be observed on a fluoroscope by the alignment of the bands 118, 119. At is is being retracted, the proximal portion of the outer shaft 106 moves within the chamber 129a of the sleeve 129, bearing against the seal 138. Advancing the collar 132 advances the outer shaft 106 back over the delivery members 108. Alternatively, the sleeve 129 could be retracted with respect to the collar 132, to withdraw the inner shaft 104. A shoulder 136 is preferably provided to limit the forward advance of the outer shaft 106.

Effective drug delivery generally requires at least 10 cc/hour at up to 45 psi. The drug delivery catheter in accordance with the present invention can deliver about 30 cc/hour at 10 psi. Drugs or agents can be delivered through the guidewire port 130 and guidewire lumen 114, as well.

In use, the catheter 100 of the invention can be advanced to the site of interest over the guidewire 112 through a guide catheter (not shown). The location of the distal end of the catheter 100 can be followed on a fluoroscope via the band 118, as is known in the art. When the catheter 100 is properly positioned within the thrombus 101, the outer shaft 106 can be retracted by withdrawing the collar 132 a sufficient distance to align the band 118 with the band 119. Initially, the delivery members 108 will remain essentially compressed by the thrombus 101. The drug or other agent is then delivered through the port 128 of the manifold 124, into the space 116 and through the catheter 100, into the grooves 110. From the grooves 110, the drug is delivered onto the surrounding thrombus 101. The delivered drugs will dissolve the portion of the thrombus 101 surrounding the delivery members 108. As the thrombus dissolves, each of the delivery members 108 will gradually flare further outward, continuing to bear against the thrombus 101 as additional drug is delivered. The thrombus 101 will thereby be dissolved evenly, from approximately the center of the thrombus 101 towards its periphery adjacent the walls of the vessel 102. Blood flow through the dissolved portion of the thrombus 101, between the delivery members 108, can resume quickly.

Depending on the length of the thrombus 101 and the length of the delivery members 108, it may be desirable or necessary to slowly withdraw the delivery members 108 through the thrombus by retracting the catheter 100 while the drug is being delivered. It may also be necessary or desirable to completely remove the delivery members 108 from the thrombus 101, compress them by the outer shaft 106, reposition the delivery members 108 within the thrombus, retract the outer shaft 106 again and resume drug delivery.

As mentioned above, additional drug delivery can be provided through the guidewire lumen 114. It may be necessary to withdraw the guidewire 112 to obtain adequate flow. Drugs or other agents delivered through the guidewire lumen 114 have been observed to follow the underside of the groove 110. It is believed that the delivery of drugs over the delivery members 108, through the grooves 110, creates a region of low pressure on the underside of the delivery members 108, which draws the delivered drug through the guidewire lumen 114.

When the thrombus is sufficiently dissolved, the outer shaft 106 can be advanced back over the distal portion of the inner shaft 104 or the inner shaft 104 can be withdrawn into the outer shaft 106. The catheter 100 can then be removed through the guide catheter. It is also possible to remove the catheter 100 through the guide catheter while it is in the deployed position.

The catheter 100 of the present invention can also be used to deliver drugs or agents to the walls of a lumen or vessel, such as to the slow flow portion of an artery. Anticoagulants and antiproliferative agents, for example, can be advantageously delivered to the site of a PTCA or PTA procedure to prevent restenosis, for example. A thrombus may be dissolved by delivering thrombolytic agents to the slow flow portion of the vessel, as well. Drug delivery through the guidewire lumen 114, could contribute to dissolution of the thrombus in conjunction with delivery to the vessel walls.

For delivery to the wall of a vessel or lumen, the delivery members 108 should preferably have a length such that when released, the delivery members will bear against the wall of the lumen or vessel at an angle. Preferably, the drug is delivered upstream of the site with respect to the blood flow so that the slow blood flow proximate the wall atraumatically carries the drug over the site. The delivered drug can travel through the distal end of the groove 110 onto the vessel wall, or over the walls 111a, 111b, themselves.

When deployed, the delivery members 108 are separated by sufficient space to allow for significant perfusion of blood between the members. This increases the possible length of surgical procedures, without requiring perfusion means which can increase the complexity of the use and manufacture of the catheter.

In addition, other devices, such as aneurysm coils or dilatation catheters, can be delivered through the catheter 100. Either the instrument can be delivered through the lumen of the inner shaft 104, or the inner shaft 104 can be completely removed from within the outer shaft 106 to enable the delivery of other such devices through the lumen of the outer shaft 106. The manifold can be easily modified to enable the insertion of such devices, as is known in the art.

To manufacture the catheter 100 of the first embodiment of the present invention, a grooved shaft 200 comprising the desired material or composition for the delivery members 108 is extruded with a length of approximately 20 cm. FIG.

5 is a front view of the shaft 200. The grooves 110 and walls 111 can be formed in the shaft through a conventional extrusion process.

The delivery members 108 are formed by cutting through the walls 111 of the extruded shaft approximately along the dotted lines 202 the desired length of the delivery members 108, here about 5.0 mm. A blade or other thin cutting device is preferred. The shaft can be cut radially or longitudinally by hand or by a machine. Radial cutting from the outside of the shaft through to the inner lumen of the shaft, is preferred. The machine can include a mounting for securing the shaft and a series of cutting blades disposed radially to simultaneously cut the distal portion of the shaft along its longitudinal axis. The number of blades corresponds to the number of delivery members desired. The thickness of the blades is preferably less than 0.010 inches. A thickness of about 0.005 inches or less is most preferred. The shaft is preferably supported on a mandrel while being cut. The shaft can be cut with a laser, as well.

As mentioned above, the length of the delivery members 108 can vary depending on the application. The length of all the delivery members is preferably the same, which enhances the ability of the members to deploy after retraction of the sleeve.

Figure 6:
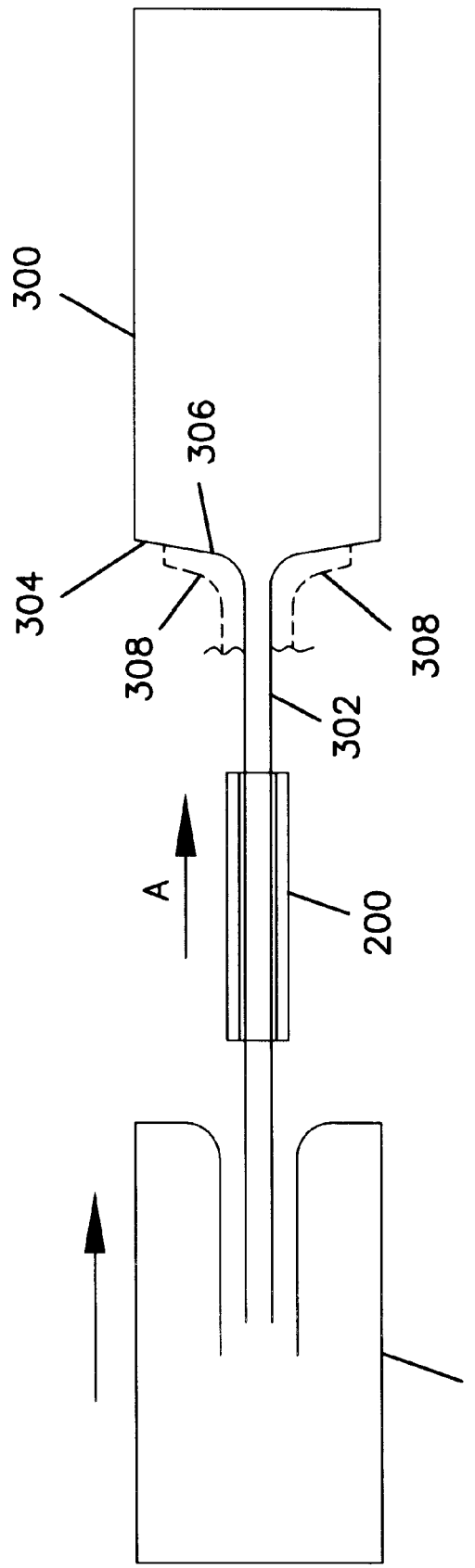
FIG. 6 illustrates several steps in the formation of the delivery members of FIG. 1.

To form the flare of the delivery members 108 in the first embodiment, a tool, such as the tool 300 shown in FIG. 6, is inserted within the guidewire lumen 114 of the extruded shaft 200, after the walls 111 are cut, as shown in FIG. 6. The tool 300 preferably comprises a rod shaped guiding mandrel or wire 302 depending essentially perpendicularly from a flat surface 304. A curved portion 306 is preferably provided between the mandrel or wire and the flat surface 304. The shaft 200 is advanced over the mandrel 302 in the direction of arrow A. As the distal ends of the delivery members 108 engage the curved surface 306, they are forced outward, along the flat surface 304, as indicated by the dotted lines 308 in FIG. 6. The tool 300 is advanced to the uncut portion of the shaft. When the tool 300 is suitably positioned with respect to the delivery members 108, a second tool 310 is preferably placed over the mandrel 302, the shaft 200 and delivery members 108 to secure the delivery members 108 against the flat surface 304. The assembly is heated in an oven or on a hot plate to about 65°–70° C. for about 30–60 seconds, to heat set the delivery members 108. In this embodiment, the angle of the flare is preferably about 90°. If a maximum flare of less than 90° is desired the tool 300 can have a conical surface instead of a flat surface, as shown in FIGS. 12–15 of U.S. Ser. No. 08/488,216, now U.S. Pat. No. 5,713,853 and U.S. Ser. No. 08/483,201, now abandoned, assigned to the assignee of the present invention and incorporated by reference herein. The second tool 310 would have a matching surface. The tools 300 can be made of brass, stainless steel or PTFE, for example.

After heat setting, the shaft comprising the delivery members is coupled to the smooth portion of the inner shaft 104 by an adhesive or thermal bonding, as is known in the art. The inner shaft can be extruded in a conventional manner.

While an outer shaft is preferred, other methods for compressing or restraining the delivery members may be provided. For example, a thread can be used to tie the delivery members together with a releasable knot. The thread can extend through a lumen of the inner shaft such as the guidewire lumen. The inner shaft would also then preferably comprise drug delivery lumens extending longitudinally through the shaft. The lumen openings at the distal end of the shaft could be aligned with the grooves of the delivery members 108, which would be attached to the distal end of the inner shaft. The use of a releasable knot to restrain expandable drug delivery members is disclosed in U.S. Ser. No. 08/488,216, now U.S. Pat. No. 5,713,853 and U.S. Ser. No. 08/483,201, now abandoned, incorporated by reference herein. That application shows multi-lumen shafts with drug delivery lumens, as well. Such multi-lumen shafts could be used with an outer shaft or sleeve to restrain the delivery members and enable drug delivery through the shaft, as well.

Figure 7:
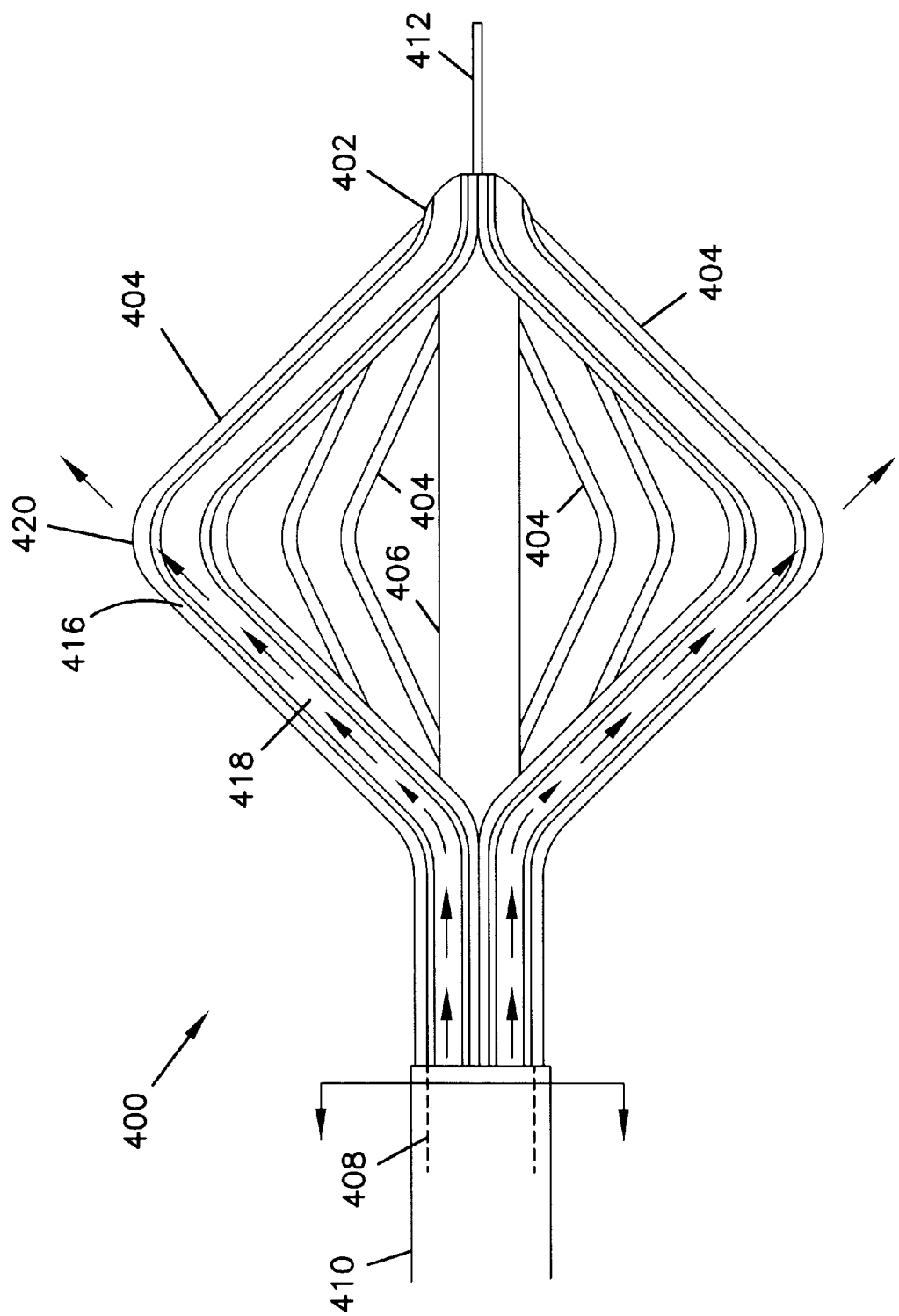
FIG. 7 is a side view of a second embodiment of the present invention in a deployed position.

FIG. 7 is a side view of a catheter 400 in accordance with a second embodiment of the present invention which does not require a retractable sheath. Here, distal portions 402 of each of the delivery members 404 are coupled to an inner shaft 406 and proximal portions 408 (shown in FIG. 8 and in phantom in FIG. 7), are coupled to an outer shaft 410. The inner shaft 406 is slidably received within the lumen of outer shaft 410. The inner shaft 406 preferably includes a lumen 416 (shown in FIG. 8) for receiving a guidewire 412.

Figure 8:
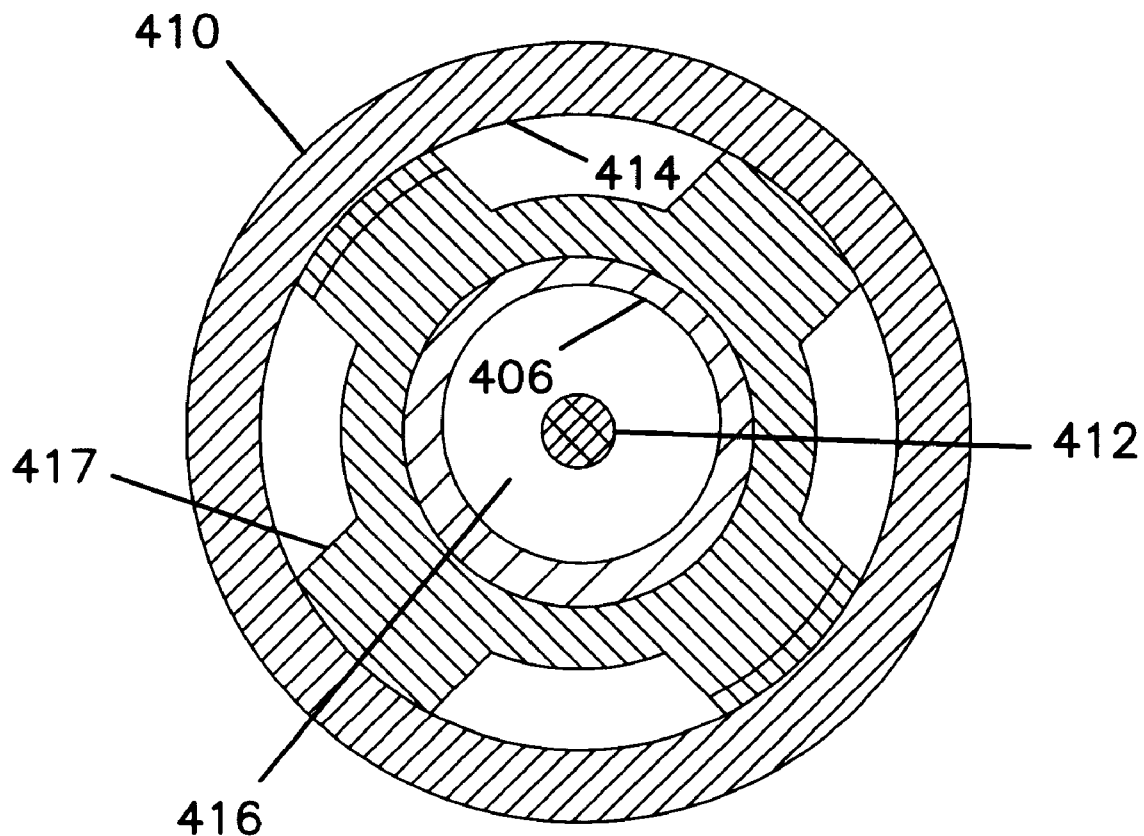
FIG. 8 is a cross-sectional view of the catheter of FIG. 7, through line 8—8.

The outer surface of the walls 417 of the grooves 418 of the proximal portions 408 of the delivery members 404 can be coupled to the inner surface 414 of the outer shaft, as shown in the cross-sectional view of FIG. 8. FIG. 8 shows the guidewire lumen 416 of the inner shaft 406, as well. As above, the coupling can be thermal or adhesive. The grooves 419 will extend into the space between the inner and outer shafts. Drugs delivered through the space will enter the grooves and be conveyed to the desired site, as indicated by the arrows in FIG. 7. The proximal portions 408 of the delivery members 404 preferably fit snugly over the inner shaft 406 to prevent leakage. The distal and proximal portions of the delivery members 404 are preferably integral.

Figure 9:
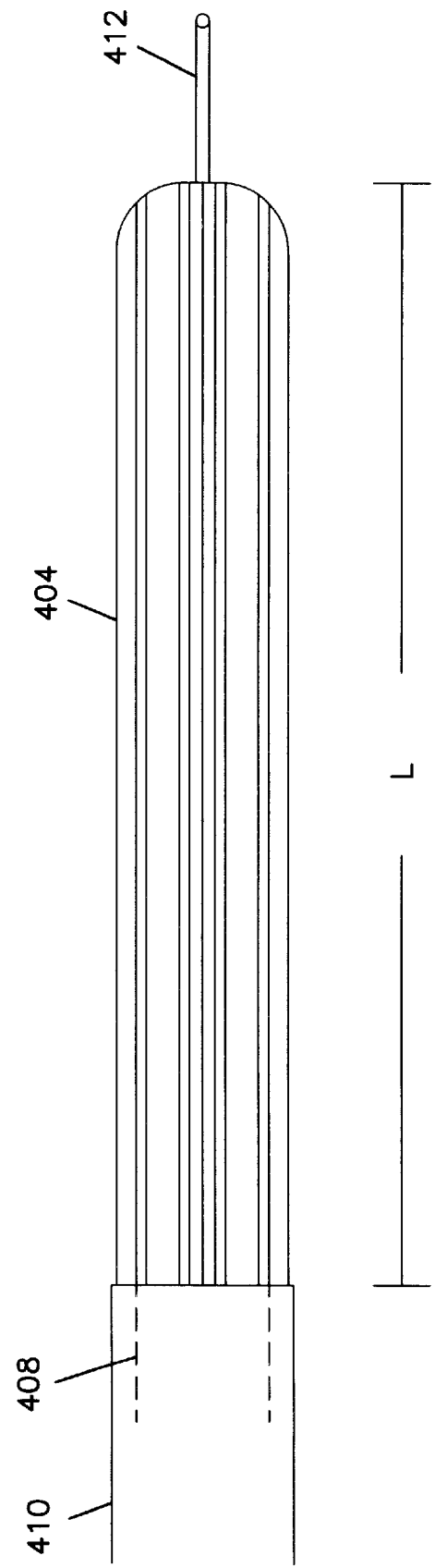
FIG. 9 is a side view of the catheter of FIG. 7, in a non-deployed position.

When not deployed, the locations of the couplings are separated by a distance L approximately equal to the length of the delivery members 404 themselves, as shown in FIG. 9. To deploy the delivery members, the inner shaft 406 is retracted or the outer shaft 410 is advanced, decreasing the distance between the couplings. As the distance between the distal and proximal portions decrease, central portions 420 of delivery members 404 buckle outward beyond the outer diameter of the outer shaft 410. When the inner shaft is fully extended again, the delivery members also become fully extended, lying adjacent to the inner shaft.

This embodiment provides positive mechanical control over the deployment and retraction of the delivery members. It also enables dilatation of the vessel wall.

The catheter 400 of this embodiment can be manufactured of the same materials as the first embodiment. To manufacture the second embodiment of the present invention, a grooved shaft with a lumen is extruded. A wire is then inserted through the lumen. A series of longitudinal cuts which do not extend to the proximal or distal ends of the shaft are then made with a cutting blade or razor through the shaft, to the lumen, to define the delivery members 404. Heat setting is not necessary. If heat setting is desired, however, an oblong shaped tool made of brass, stainless steel or PTFE, for example, can be inserted between the ribs. A perspective view of such a tool is shown in U.S. Ser. No. 08/488,216, now U.S. Pat. No. 5,713,853 and U.S. Ser. No. 08/483,201, now abandoned, assigned to the assignee of the present invention and incorporated by reference, herein. A cross-sectional view of the tool is shown in those applications. The tool preferably includes an opening along its longitudinal axis for receiving a wire inserted through the distal end of the shaft. The wire helps to maintain the tool centered between the ribs. The shaft and tool can then be heated in an oven.

Examples of drugs or agents which can be delivered through the catheters and methods of the present invention include substances which inhibit platelet deposition and thrombus formation or promote thrombolysis and thrombus dissolution, such as plasmin, tissue plasminogen activator (tPA), single chain prourokinase (scuPA), prostaglandins, cyclooxygenase inhibitors, phosphodiesterase inhibitors, thromboxane synthetase inhibitors; antagonists of glycoprotein receptors including (GP) Ib, GP IIb/IIIa, antagonists of collagen receptors, and antagonists of platelet thrombin receptors, for example.

Alternatively, the drugs or agents delivered by the systems and methods of the present invention can directly affect platelet metabolic function. Examples of such substances include prostaglandins, cyclooxygenase inhibitors, phosphodiesterase or thromboxane synthetase inhibitors, inhibitors of calcium transport, or elevators of cyclic adenosine monophosphate (cyclic AMP).

Examples of anticoagulants which can be delivered by the catheters and methods of the present invention include heparin, hirudin, hirulog, hirugen, activated and non-activated protein C, synthetic or naturally occurring antagonists of thrombin, and Factor Xa, or other activated or non-activated coagulation protease inhibitors and coagulation factors, e.g., FIX, FVIII, FV, FVIIa and tissue factor.

Examples of antiproliferatives which can be delivered by the catheters and methods of the present invention include dexamethasone, growth factor, a growth factor inhibitor, growth factor receptor antagonist, transcriptional repressor, translational repressor, antisense DNA, antisene RNA, replication inhibitor, inhibitory antibodies, antibodies directed against growth factors or their receptors, bifunctional molecules comprising a growth factor and a cytotoxin, bifunctional molecules comprising an antibody and a cytotoxin.

Polaxymer 188, another antiproliferative, can also be delivered in accordance with the present invention to pave or line the walls of an artery to prevent smooth muscle growth.

The agent delivered by the catheters and methods of the present invention can also be a vasodilator, such as nitroglycerin, nitroprusside or other nitric oxide liberators. The vasodilator can also include other suitable vasoactive agents such as beta receptor blocking drugs, inhibitors of intracellular calcium transport, prostaglandins, thromboxane antagonists, and the like.

Other cardiovascular applications can include the delivery of medical grade cyanoacrylides for the treatment of aneurysms, arterial venous fistulas, or carotid cavernous fistulas. Polyvinyl alcohol products can be delivered to treat arterial venous malformations. Papavarine, available from Eli Lilly & Co., can be delivered to treat cerebral vasospasam.

The catheters and methods of the present invention are also applicable wherever it would be desirable to deliver drugs or other agents within a lumen or vessel. For example, another procedure in which the present invention could be used is to deliver anesthesia to the prostate during treatment of benign prostate hypertrophy (BPH). The catheters and methods of the present invention can be used to deliver drugs or other agents to the urethea, bladder, rectum, bile duct, pancreatic duct and central nervous system, such as along the spinal cord, for example, as well.

The above embodiments are examples of systems and methods of the present invention, which are defined in the following claims.

I claim:

1. A catheter for delivering drugs or other agents within lumen, comprising:

an outer shaft having a lumen extending longitudinally therethrough, an inner shaft slidably received within the lumen of the outer shaft, the inner shaft having a distal portion and a proximal portion, the distal portion comprising a plurality of flexible resilient delivery members, at least one of the delivery members comprising at least one external groove thereon for delivery, the delivery members having a non-deployed position compressed by the outer shaft when the delivery members are within the outer shaft and a deployed position when the delivery members extend beyond the outer shaft, wherein in the deployed position the delivery members flare outward beyond the outer shaft at an angle; and the inner and outer shafts defining a space between them through which the drug or agent is conveyed to the grooves of the delivery members.

2. The catheter of claim 1, wherein the delivery members are attached to the inner shaft.

3. The catheter of claim 2, wherein the delivery members are softer than the proximal portion of the inner shaft.

4. The catheter of claim 3, wherein the proximal portion of the inner shaft is smooth.

5. The catheter of claim 1, wherein the angle is acute.

6. The catheter of claim 1, wherein the angle is essentially a right angle.

7. The catheter of claim 1, wherein the inner shaft further comprises a guidewire lumen.

8. The catheter of claim 1, wherein the outer shaft comprises a proximal portion and a distal portion, the distal portion is softer than the proximal portion.

9. The catheter of claim 1, wherein the proximal portion of the inner shaft is smooth.

10. The catheter of claim 1, wherein the inner shaft further comprises a grooved portion adjacent the distal portion, extending to and aligned with the at least one groove of the delivery members.

11. A catheter for delivering drugs or other agents to a site within a lumen, comprising:

a delivery portion comprising a first shaft having a distal portion and at least one flexible resilient delivery member at the distal portion, the at least one delivery member comprising at least one external groove thereon for delivery, wherein the at least one delivery member has a deployed position for bearing against the site and a non-deployed position for not bearing against the site;

means for deploying the at least one delivery member from the non-deployed position to the deployed position, the means for deploying including a second shaft having a lumen extending longitudinally therethrough, the first shaft being received in the lumen, the at least one delivery member being in the non-deployed position when the at least one delivery member is received within the lumen and compressed by the second shaft; and means for conveying a drug or agent within the second shaft, to the at least one delivery member.

* * * * *